United States Patent [19]
Spichiger-Keller et al.

[11] Patent Number: 5,928,957
[45] Date of Patent: Jul. 27, 1999

[54] DETERMINATION OF ANALYTE CONCENTRATION BASED ON A MICELLAR RECOGNITION SYSTEM AND STRUCTURED LAYERS THEREFOR

[75] Inventors: Ursula Spichiger-Keller, Au-Wädenswil; Eva Vaillo, Zürich, both of Switzerland

[73] Assignee: AVL Medical Instruments AG, Schaffhausen, Switzerland

[21] Appl. No.: 08/547,596

[22] Filed: Oct. 24, 1995

[30] Foreign Application Priority Data

Oct. 24, 1994 [CH] Switzerland .............. 3181/94

[51] Int. Cl.⁶ .................................. G01N 33/543
[52] U.S. Cl. .......................... 436/518; 435/5; 435/7.21; 435/7.32; 435/7.4; 435/969; 436/514; 436/528; 436/535; 436/829; 436/71
[58] Field of Search ............... 435/5, 7.21, 7.32, 435/7.4, 969; 436/514, 518, 528, 535, 71, 829

[56] References Cited

U.S. PATENT DOCUMENTS 4,939,098  7/1990  Suzuki et al. ..................... 436/514

OTHER PUBLICATIONS

A.V. Kabanov et al., "A New Way in Homogeneous Immunoassay: Micellar Systems as a Medium for Analysis" in Anal. Biochem. 181, 145–148 (1989).
K. Martinek et al., "Micellar Enzymology" in Eur. J. Biochem. 155, No. 3, 453–468 (1986).

*Primary Examiner*—Christopher L. Chin
*Attorney, Agent, or Firm*—Watson Cole Grindle Watson, P.L.L.C.

[57] ABSTRACT

Starting from two non-miscible phases, i.e., a lipophilic and a hydrophilic phase, a surface-active substance and a recognition component, a micellar recognition system is built in a suitable manner and is incorporated into a layer structure. The micellar recognition system is provided in a single thin layer in which the recognition component is distributed homogeneously. Additional layers which may be provided about this layer, have an influence on the properties of the entire layer structure. On contact between the layer structure and the substance to be measured a recognition step takes place in the layer which is followed by a transducing step. In this way a measurement variable is produced by means of which information is obtained on the substance. The layer structures exhibit higher sensitivity, a lower detection threshold, short response time and special robustness with regard to sample interference.

8 Claims, 3 Drawing Sheets

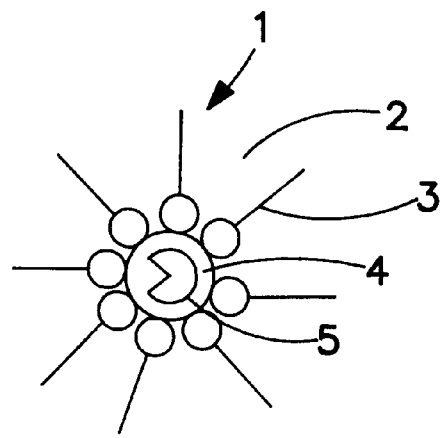
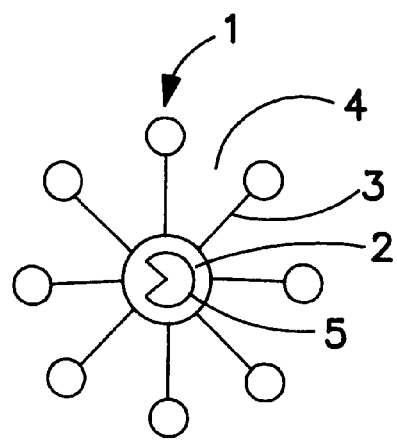
FIG. 2  FIG. 3
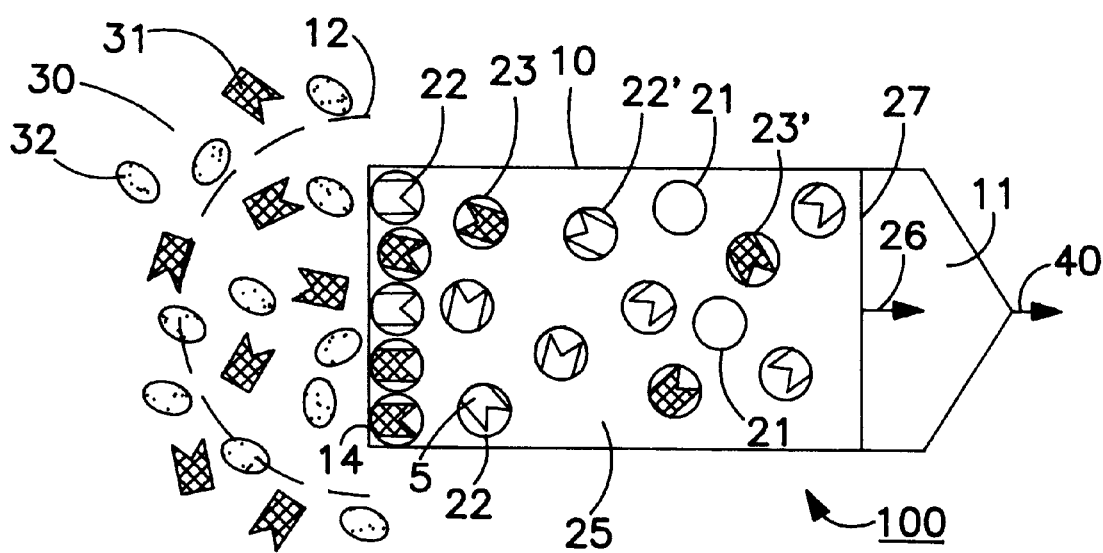
FIG. 4

//5,928,957//

DETERMINATION OF ANALYTE CONCENTRATION BASED ON A MICELLAR RECOGNITION SYSTEM AND STRUCTURED LAYERS THEREFOR

BACKGROUND OF THE INVENTION

This invention relates to a method, application of the method and a layer structure for determination of a substance.

Chemical sensors for the determination of chemical substances (so-called analytes) in samples or specimens comprise a whole range of thermodynamically reversible or regenerable measuring probes. Such probes must include at least one recognizing element, at least one transducer element, and, ideally, at least one calculation/display element. The recognizing element usually is implanted in a layer structure; the analyte is selectively isolated from other substances in the sample/specimen and extracted into the layer. Recognition molecules are also referred to as host molecules and are capable of selectively recognizing the analyte, which may be referred to as guest molecule. The process of recognition, the interaction between host and guest molecule, leads to a quantifiable signal which is obtained in a transducing process. Biosensors represent a subgroup of chemical sensors in which the recognizing element is a biologically active substance, such as enzymes, peptides, receptors, antibodies, cell organelles, etc.

Chemical sensors and biosensors feature a growing development potential and are of increasing importance in analytics (analyses in the fields of environmental and food technology, medicine and biotechnology). The characteristics of such sensors are:

inexpensive and rapid analyses, continuous measuring directly in the specimen, mobility of probes and measuring systems, use in isolated locations and high-risk sites, selective use of specifically tailored systems.

2. Description of the Prior Art 2.1 Recognition molecules

Chemical recognition molecules as such are synthetic substances that are specifically designed for this purpose (W. Simon, U. E. Spichiger, Development and Application of Ion-Selective Electrodes, International Laboratory, September 1991, 35–43). In biosensors, on the other hand, molecules are used which are already known from biological processes, or are produced in biological systems. Some of them are enzymes, synthetic and gene-manipulated enzymes; antibodies, fragments of antibodies, synthetic and gene-manipulated antibodies; receptors and their hybrids; peptides, carbohydrates, lipids and their hybrids.

2.2 Design of sensors

As is known recognition molecules are implemented in the chemical probe in two different ways:

2.2.1 by immobilization on the surface of the supporting medium (electrostatic, covalent, and adhesive interactions, etc.); they may be brought into contact with both nonpolar and polar phases (Hall, G. F., Turner, A. P. F., J. Cell. Biochem., Suppl. 14B (1990) 345; Hall, G. F. et al., Anal. Chim. Acta 213 (1988) 113–119).

2.2.2 by incoporation into polar or nonpolar bulk membranes, so that molecular recognition takes place in or next to the boundary face rather than on the surface of the membrane. Relevant examples have been described in various publications (Seiler, K., Simon, W., Anal. Chim. Acta, 266 (1992) 73–87; patent publications EP-A-0153641, JP-A-2082152).

In the transducing process the step of chemical recognition is converted into a physical measurement variable. In the instance of optodes (optical sensors) the measurement variable is an optical signal, in the instance of electrodes (electro-chemical sensors) an electrical signal.

2.3 Existing sensors

Chemical sensors and biosensors are used for quantitative analysis of various analytes, such as 2.3.1 for ions and charged molecules ion-selective electrodes potentiometric electrodes ion-selective optodes 2.3.2 for uncharged, charged, or neutral molecules optodes amperometric, enzymatic electrodes biosensors, immunosensors 2.4 Problems and drawbacks of existing sensor systems As regards sensors in which the recognition molecule is immobilized on the surface (cf. 2.2.1) and exposed to the sample, the environment of the recognition process is poorly defined. As a rule the quality obtained in such instances does not meet the demands that are made on a reliable sensor. Typical deficiencies concern the life of the sensor, its invariance to pH, proteins, general nonspecific influences exerted by the matrix of the specimen or sample and ionic strength. Nonspecific interactions occur with the background of the sample/specimen. Regeneration of the recognition layer leads to the loss of expensive compounds, such as antigens and antibodies.

As regards sensors in which the recognizing molecule is implanted in a layer structure (cf. 2.2.2), the above drawbacks are not encountered. In this type of biosensors, however, the transducer layer usually is separated from the recognition layer. As a consequence, part of the signal is lost by diffusion; response time increases and the signal yield is reduced, as is described by Stamm for the urea optode (C. Stamm et al., Anal. Chim. Acta, 282 (1993), 229–237).

It is further known that biomolecules are solubilized in organic solvents by means of reverse micelles while retaining their biological activity (Luisi, P. L. et al., Methods in Enzymology, Vol. 136 (1987) 188–216, Acad. Press Inc.; Martinek, K. et al., Eur. J. Biochem. 155 (1986) 453–468). The three-component systems described comprise a tenside, and a polar hydrophilic, and a nonpolar lipophilic solvent; they are characterized by a parameter $W_o$ representing the ratio of water as polar solvent to tenside. The functionality of the enzymes solubilized therein was examined in dependence on the water content (Han, D. et al., Biocatalysis, Vol.4 (1990), 153–161).

SUMMARY OF THE INVENTION

It is an object of the present invention to propose methods and layer structures for the determination of substances, where a micellar recognition system is formed and incorporated into a layer structure. When the substance to be determined is brought into contact with the layer structure, a recognition step takes place, which is followed by a transducing step leading to the generation of a measurement variable. With the use of this measurement variable, the desired information on the substance is obtained.

The approach of incorporating the recognition component in a micellar system and thus constructing a micellar recognition system will largely eliminate the drawbacks listed in section 2.4. The amphiphilic character of these systems will permit combination of the previously known recognition and transducer layers into one single layer.

The terminology used in the context of the invention is as following.

3. Terminology

3.1. Substance

Substances are all neutral (uncharged or zwitterionic) and charged compounds, as well as radicals and isotopes on which information is to be obtained.

3.2 Recognition component

Recognition components are compounds that have a specific interaction with the substance to be determined or the host molecule.

3.3 Micellar system

A micellar system is a system which comprises three components in a defined quantitative ratio. The three components are a lipophilic phase, a hydrophilic phase, and at least one surface-active substance.

3.4 Micellar recognition system

A micellar recognition system is the combination of at least one recognition component (3.2) and a micellar system (3.3).

3.5 Recognition step of the first kind

A recognition step of the first kind is a step in which selective interaction takes place between the substance and the recognition component.

3.6 Recognition step of the second kind

A recognition step of the second kind is a step in which the recognition step of the first kind leads to a further reaction, which is conditionally selective, with another recognition component.

3.7 Transducing step

A transducing step is a step or a sequence of steps in which the recognition step of the first kind, either directly or via one or several recognition steps of the second kind, leads to a quantifiable measurement variable, each of the recognition steps of the second kind being part of the transducing process.

3.8 Layer structure

In a layer structure one single layer is formed by combination of the recognition step of the first kind (3.5) and the transducing step (3.7), the latter taking place, at least partly, in this single layer. The addition of auxiliary layers for purposes such as ion exclusion, improvement of biocompatibility, or enhancement of gas permeability, is permitted. By combining these layers a layer structure is obtained.

3.9 Cocktail

A cocktail is a mixture of the components of the micellar recognition system (3.4) and at least one auxiliary agent.

BRIEF DESCRIPTION OF THE DRAWINGS

Following is a more detailed description of the invention as illustrated by the accompanying drawings, in which FIG. 2 is a schematical representation of a micellar recognition system with reverse micelles, FIG. 3 is a schematical representation of a micellar recognition system with normal micelle arrangement, FIG. 4 is a schematical representation of the incorporated micellar recognition system as a layer of a layer structure prepared by procedure A.

DETAILED DESCRIPTION OF PREFERRED EMBODIMENTS

The method of the invention is described in greater detail below, with reference to the flow chart in FIG. 1 indicating the general steps. For the description of the individual steps of the process, the corresponding reference numbers of the flow chart are used.

4. Flow chart

Figure 1:
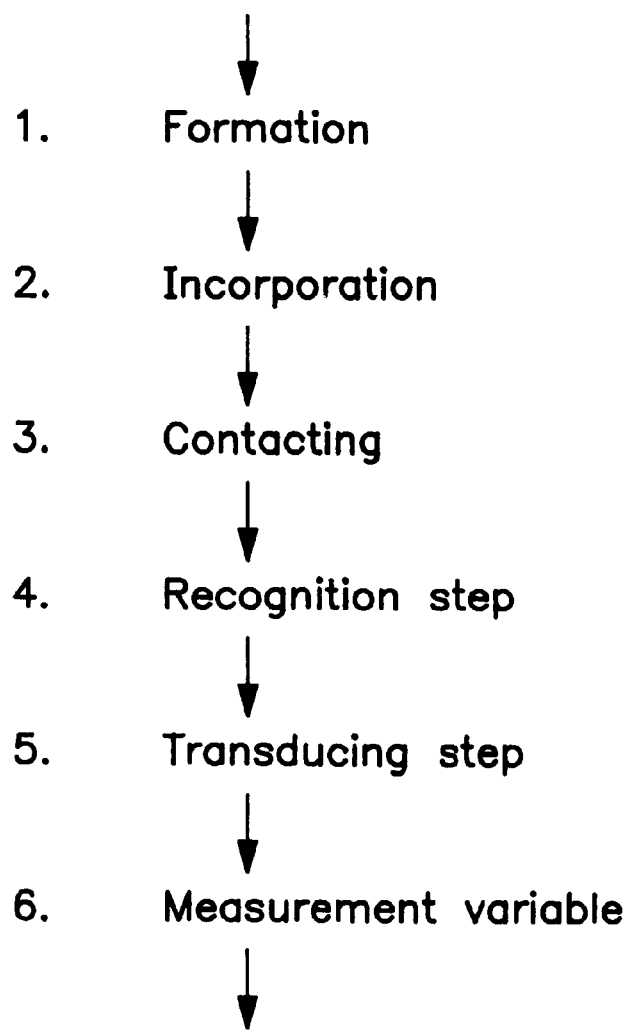
FIG. 1 is a flow chart of a method for determination of a substance.

FIG. 1 represents the flow chart of a method for determination of a substance, which is described below by steps 1 to 6.

Components of the micellar recognition system

The micellar recognition system is basically composed of a micellar system and one or more recognition components. If only one recognition component is provided, a recognition step of the first kind will ensue, as will be described in detail below. If several recognition components are provided, they will usually lead to recognition steps of both the first and second kind. The components of a micellar recognition system are:

Two non-miscible phases, one of which has a lipophilic character and the other one a hydrophilic character;

(1) The lipophilic phase has a low polarity and may be an organic solvent, such as tetrahydrofurane, cyclohexane, cyclohexanone, etc; any mixtures of organic solvents, etc.; a plasticizer, a polymer, silicone fluid, methylene chloride.

(2) The hydrophilic phase comprises solvents of higher polarity, such as $H_2O$, aqueous buffer solutions, $H_2O$-miscible solvents, such as acetonitrile; or hydrogels.

Together, the two non-miscible phases are designed to fulfill the following two functions essential for matching the two phases against each other: they define the extraction properties and act as solvents of the components. Together they control the viscosity of the layer to be formed. They determine the localization of the solubilized components, i.e., the distribution of the components between the two phases.

(3) A surface-active substance of natural or synthetic origin, which may comprise several components: tensides and detergents of all kinds, e.g., ionic compounds, such as AOT (sodium-(2-ethylhexyl)-sulphosuccinate), CTAB (cetyl-trimethyl-ammoniumbromide); nonionic, such as Brij, Tween 85, Triton X-100; zwitterionic, such as lecithins, betains, aminoxides, etc.

(4) At least one recognition component, which may already be regarded as hydrophilic phase in certain instances, provided it contains a sufficient amount of $H_2O$, such as the hydration sheath of an enzyme, for example.

Recognition components may be synthetic or partially synthetic products, they may be designed by means of models, or exist as natural products. Examples include enzymes, synthetic and gene-manipulated enzymes; antibodies, fragments of antibodies, synthetic and gene-manipulated antibodies; receptors and their hybrids, synthetic and gene-manipulated receptors; peptides, carbohydrates, lectins, lipids and their hybrids, synthetic ligands, complex-, clathrate- and associate-forming agents, carriers, chromoionophores, ionophores, redox dyes, pH indicators and macromolecules, organs, organelles, microorganisms.

Depending on whether the hydrophilic or the lipophilic phase is predominant, normal micelles or reverse micelles are formed in the instance of a tenside concentration greater than CMC (Critical Micelle Concentration). The size of the reverse micelles is determined by the molecular ratio $W_o$ of water to tenside ($W_o=[H_2O]/[\text{tenside}]$). If the water content increases, water-in-oil microemulsions (w/o microemulsions) are obtained, and if the polar phase predominates, oil-in-water microemulsions (o/w microemulsions).

1. Formation of the micellar recognition system

The micellar recognition system may be prepared in several ways, by conveniently combining the mixture of the four components referred to above. For practical reasons, preference is usually given to the procedures listed below, although many other procedures would be possible, which are not discussed in the context of this paper.

Procedure A (a) Formation of a first mixture from components 1 and 3, i.e., a lipophilic phase and a surface-active substance.

(b) Formation of a second mixture from components 2 and 4, i.e., a hydrophilic phase and a recognition component.

(c) Combination of the first and second mixture at a given ratio $W_o=[H_2O]/[tenside]$ and subsequent mixing.

(d) Vortex (centrifugal vibration mixer) until micelle formation, i.e., until a clear, homogeneous phase is obtained.

Procedure B (a) Formation of a first mixture from components 1, 2, 3, i.e., a lipophilic phase, a hydrophilic phase, and a surface-active substance, at a given ratio $W_o$.

(b) Vortex (centrifugal vibration mixer) until micelle formation, i.e., until a clear, homogeneous phase is obtained.

(c) Formation of a second mixture from the first mixture provided as a clear and homogeneous phase, by adding component 4, i.e., a recognition component.

(d) Stirring of the second mixture until a homogeneous distribution is obtained.

Procedure C (a) Formation of a first mixture from components 1, 3, 4, i.e., a lipophilic phase, a surface-active substance and a recognition component leading to a recognition step of the second kind.

(b) Formation of a second mixture from components 2 and 4, i.e., a hydrophilic phase and a recognition component leading to a recognition step of the first kind.

(c) Combination of the first and second mixture at a given ratio $W_o=[H_2O]/[tenside]$ and subsequent mixing.

(d) Vortex (centrifugal vibration mixer) until micelle formation, i.e., until a clear, homogeneous phase is obtained.

Procedure D (a) Formation of a first mixture from components 1, 3, 4, i.e., a lipophilic phase, a surface-active substance and two recognition components, both of which lead to a recognition step of the second kind.

(b) Formation of a second mixture from components 2 and 4, i.e., a hydrophilic phase and a recognition component leading to a recognition step of the first kind.

(c) Combination of the first and second mixtures at a given ratio $W_o=[H_2O]/[tenside]$ and subsequent mixing.

(d) Vortex (centrifugal vibration mixer) until micelle formation, i.e., until a clear, homogeneous phase is obtained.

If several micellar recognition systems are to be formed the same or any desired combination of procedures may be employed.

2. Incorporation of the micellar recognition system into a layer structure

The micellar recognition system may be incorporated into a layer structure in several ways.

2.1 A viscosity-controlling additive is dissolved in the lipophilic phase of the micellar recognition system to ensure the required physical properties of the layer to be fabricated.

Suitable materials for this purpose are polymers and copolymers both natural and synthetic, such as polyvinyl chloride (PVC) and its derivatives (PVC-OH, PVC-CH$_2$OH, PVC-NH$_2$, PVC-NHR, PVC-COOH), polystyrene, poly (styrene-butadiene), polyurethanes, polyamides, acrylates, polymethacrylates, poly-(vinylisobutyl ether), organosilicates, silicones. In other instances in-situ polymerizations may take place, such as photopolymerizations, electropolymerizations, or polymerizations departing from a monomer and an initiator. For this purpose silanes, siloxanes, acrylates, urethanes are used, for example. Other suitable materials are gelling agents such as gelatine, pectin, bentonite, etc.

2.2 In order to obtain the required chemical and physical properties of the layer, plasticizers may be added to the mixture (2.1) as solvents. Such plasticizers usually are low-molecular, liquid organic substances that are non-volatile at room temperature, such as esters of organic and inorganic acids, alcohols, ethers, ketones, sulfonamides, halogenated hydrocarbons, and others. Typical examples are bis(2-ethylhexyl)sebacate (DOS), ortho-nitrophenyloctylether (o-NPOE) and derivatives, bis(2-ethylhexyl)phthalate or adipate, bis(1-butyl pentyl)adipate (BBPA).

2.3 Further auxiliary agents and additives may be added to the mixture (2.2) to build up the layer. They are required, for example, to maintain electroneutrality, for catalysis or buffering, or to obtain a certain solubility.

2.4 The mixture (2.3) of the micellar recognition system obtained in steps 2.1 to 2.3 is referred to as cocktail. Such a cocktail exhibits a suitable viscosity permitting optimum processing and handling. Usually the viscosity is quite low. If this is not the case, optimum viscosity for application of the cocktail on a support is obtained by the addition of a highly volatile solvent.

2.5 The cocktail is applied on a suitable support in a conventional manner, either with a dropper or by means of spin-on equipment. By complete evaporation of the organic solvent and a subsequent drying process, a layer is obtained in which the micellar recognition system is provided. It should be noted that this single layer includes all components for the recognition step of the first kind and the transducing step side by side, without affecting the stability of the recognition component.

If several micellar recognition systems are provided, they may be combined in a single cocktail and thus give a single layer, or the micellar recognition systems are processed in different cocktails to produce several single layers in sequence.

2.6 For the design of the layer structure, auxiliary layers may be added to the layer or layers obtained in 2.5, such as TECOFLEX (medical grade aliphatic thermoplastic polyurethanes made by Thermedics, Inc.), NAFION (perfluorosulfonated hydrocarbon polymer made by Du Pont de Nemours & Co., Inc.), etc. These additional layers are used to improve biocompatibility, mechanical stability, or to increase the life of a structure, or they serve as a diffusion barrier, or as a general buffering layer for substrates, products, or H$^+$-activity. The layer structure may also be in contact with several supports with different functions.

3. Contacting the substance with the layer structure

The layer structure obtained in step 2 is brought into contact with the substance. The substance may be provided in a liquid or gaseous phase; it may be analyzed directly in the specimen or in a prepared sample. Examples of uncharged substances are urea, creatinine, tensides, alcohols, acetone, glucose, carbohydrates, glycols, silicones, polymers, pigments, pesticides, herbicides, acaricides; hormones, such as glucagon, insulin, serotonin, adrenaline, steroids; neurotransmitters, such as serotonin, adrenaline, acetylcholine, DOPA; gases, aromatic and aliphatic hydrocarbons, and metalorganic compounds. Neutral molecules include certain amino acids, peptides, and proteins. Typical ions are $H^+$, $Li^+$, $K^+$, $Na^+$, $Rb^+$, $Cs^+$, $Ba^{2+}$, $Mg^{2+}$, $Ca^{2+}$, $Sr^{2+}$, $Cu^{2+}$, $NH_4^+$, $Cl^-$, $ClO_4^-$, $H_2PO_4^-$, $HPO_4^{2-}$, $PO_4^{3-}$, $HAsO_4^{2-}$, $H_2AsO_4^-$ $AsO_4^-$, $HSeO_3^-$, $SeO_4^{2-}$, $SO_3^{2-}$, $HSO_3^-$, $SCN^-$, $CN^-$, $WO_4^{2-}$. Other charged compounds are silicates, organic molecules, such as sulphonates, phosphonates, metalorganic compounds and metal complexes, etc.; metabolites, substrates and drugs, such as heparin, protamine, choline, phosphatides, organic acids, carboxylates, such as acetate, acetoacetate, oxalate, γ- and β-hydroxybutyrate, δ-aminolaevulinic acid, salicylates, phenolates, protonated amines, ammonium compounds, alkaloids, optically active and helical compounds, DNA, RNA, receptors, microorganisms, viruses, organelles, isotopes, etc.

It has been found unexpectedly that the micellar recognition system equilibrates in the viscous system with the substance in the sample, i.e., the equilibrium or steady state is achieved sufficiently fast. The system is thus suitable for use in analyses.

4. Recognition step of the first kind

During contacting the substance to be determined is extracted into the layer structure and reacts selectively with the recognition component in the single layer. If the amount, concentration and activity are the same, the substance is preferred by a factor usually given as log K, base 10 logarithm of the overall distribution coefficient, whereas other substances are discriminated by this factor. Depending on the type of interaction (cf. Terminology, 3.5, 3.6) the substance may be reacted into further products. Interaction may take place in the form of complex formation, redox processes, addition reactions, association and dissociation, formation of inclusion compounds (clathrates), hydrolysis, group-, proton- and electron-transfer reactions, ionic exchange, etc.

5. Transducing step

As a consequence of molecular recognition in step 4, a measurement variable is produced. This variable either may be directly quantified or it may be converted into a measurable quantity by coupling it to one or more recognition steps of the second kind. The transducing step may be effected by transfer of photons, electrons or mass, by electron transitions, via excited states. Signal detection may be effected by photometric, potentiometric, amperometric, voltammetric, polarographic, coulometric or conductometric methods, or by countings, measurements of decay times, fluorescent life, reaction rate, relaxation times, pH changes, etc. Changes in viscosity, force, mass, dispersion, frequency, dielectric properties (permittivity), polarization plane, rotational velocity, angle, also may be used for transducing.

In the course of the transducing step, recognition steps of the second kind may take place as a consequence of the recognition step of the first kind. Recognition steps of the second kind are due to interactions between the products of the recognition step of the first kind and further recognition components, or to being induced by the recognition step of the first kind.

Whereas the recognition components leading to a recognition step of the first kind must have a selective character, this is not essential for recognition components leading to a recognition step of the second kind.

If several micellar recognition systems are provided, each micellar recognition system will lead to a transducing step; the individual transducing steps need not differ from each other.

6. Measurement variable

The measurement variable obtained in the transducing step 5 may vary greatly, concerning a change in absorption, current, potential, conductivity, refraction index, temperature, viscosity, dispersion, polarization, frequency, or others. From this variable information on the substance is obtained either directly or by mathematical operations, with reference to amount, concentration, activity, etc.

The measurement variable thus supplies information on the target substance, which either is displayed on a display unit, for example, or kept available for further processing in analog or digital form. For instance, the measurement variable could be processed via an optical waveguide or a semiconductor element, which will not be further discussed in the context of this paper. The transducing step could also lead to several measurement variables at the same time, which may be obtained by a single micellar recognition system or several micellar recognition systems.

FIG. 2 is a schematical representation of a micellar recognition system with reverse micelles. The layer structure is represented by layer 1, which comprises a lipophilic phase 2, a surface-active substance 3, a hydrophilic phase 4, and a recognition component 5. The recognition component 5 is provided in the hydrophilic phase 4 in aqueous solution, for example. The surface-active substance 3 surrounds the hydrophilic phase 4 so that it encloses the area of the hydrophilic phase as a reverse micelle, thus effectively screening the recognition component dissolved in the hydrophilic phase from undesirable influences of the lipophilic phase 2. The recognition component may partly project into the adjacent phase. With this kind of screen denaturation of the recognition component is avoided and the life, solubility and distribution or dispersion of the recognition component is improved. Such a micellar recognition system could also exhibit reverse micelles without recognition components, so-called empty micelles.

FIG. 3 is a schematical representation of a micellar recognition system with normal micelle arrangement. The layer structure is represented by layer 1, which comprises a hydrophilic phase 4, a surface-active substance 3, a lipophilic phase 2 and a recognition component 5. The recognition component 5 is provided in the lipophilic phase 2 in a bis(2-ethylhexyl)sebacate (DOS) solution, for example. The surface-active substance 3 surrounds the lipophilic phase 2 so that it encloses the area of the lipophilic phase as normal micelles, thus effectively screening the recognition component dissolved in the lipophilic phase from undesirable influences of the hydrophilic phase 4. The recognition component may partly project into the adjacent phase. Such a micellar recognition system could also exhibit micelles without recognition components, so-called empty micelles.

FIG. 4 is a schematical representation of the incorporated micellar recognition system as a layer in a layer structure prepared by procedure A. A layer 10 is surrounded by a support 11 on one side and by an auxiliary layer 12 on the other side. The layer 10, the support 11 and the auxiliary layer 12 together form a layer structure 100. Layer 10 is composed of empty micelles 21, unoccupied micelles 22 and 22', and occupied micelles 23 and 23', and of phase 25 surrounding the micelles, which is almost entirely free from the volatile solvent. A sample 30 comprising a substance 31 and other components of which only a discriminated substance 32 is shown, is brought into contact with the layer structure 100, the sample 30 being located on the side of layer 10 opposite of the support 11. Auxiliary layer 12 is also located on the side of layer 10 opposite of the support 11, and is largely permeable, or semipermeable to specific sample components.

Empty micelles 21 of layer 10 are micelles which do not contain a recognition component 5 when the layer is formed, but which are part of the micellar system.

Unoccupied micelles 22 and 22' contain a recognition component 5 and thus are a component of the micellar recognition system. While the unoccupied micelle 22 practically encloses the recognition component 5, the recognition component 5 in the unoccupied micelle 22' partly projects into the adjacent phase. Unoccupied micelles 22 and 22' are part of the micellar recognition system before interaction between the substance 31 and the recognition component 5.

Occupied micelles 23 are part of the micellar recognition system after interaction between the substance 31 and the recognition component 5.

At the site exposed to the sample 30 the layer 10 has a reactive region 14 in which are provided the empty micelles 21, unoccupied micelles 22 and occupied micelles 23.

Following is a description of the functioning of the micellar recognition system. When the substance 31, which is part of the sample 30, is brought into contact with the reactive region 14, the substance is recognized selectively by the micellar recognition system; this is represented by a recognition step of the first kind and micelles 23. The discriminated substance 32 is not or barely recognized by the micellar recognition system, which makes the method highly selective. The sample 31 and the layer 10 principally are two non-miscible phases. In the occupied micelles 23 and 23' the substance 31 from sample 30 is homogeneously distributed over the entire layer 10 in dependence on time. The same applies to empty and unoccupied micelles and other components of the layer. Distribution is effected quickly as a rule, since the layer 10 is thin, i.e., typically smaller than 50 micrometers. After molecular recognition has taken place in the recognition step of the first kind, the transducing step takes place next, in which a measurement variable is produced. By modification of the number of occupied micelles, the measurement variable forms as a change in a physical property, such as refraction index, temperature, etc. (cf. step 6). At an interface 27 between the layer 10 and the support 11 a measurement variable is produced, which is indicated by arrow 26 in the drawing. The measurement variable represents an optical signal, if the support is configured as an optical waveguide. In this way the measurement variable is converted into an information signal 40, which can be processed or further utilized as such.

Figure 5:
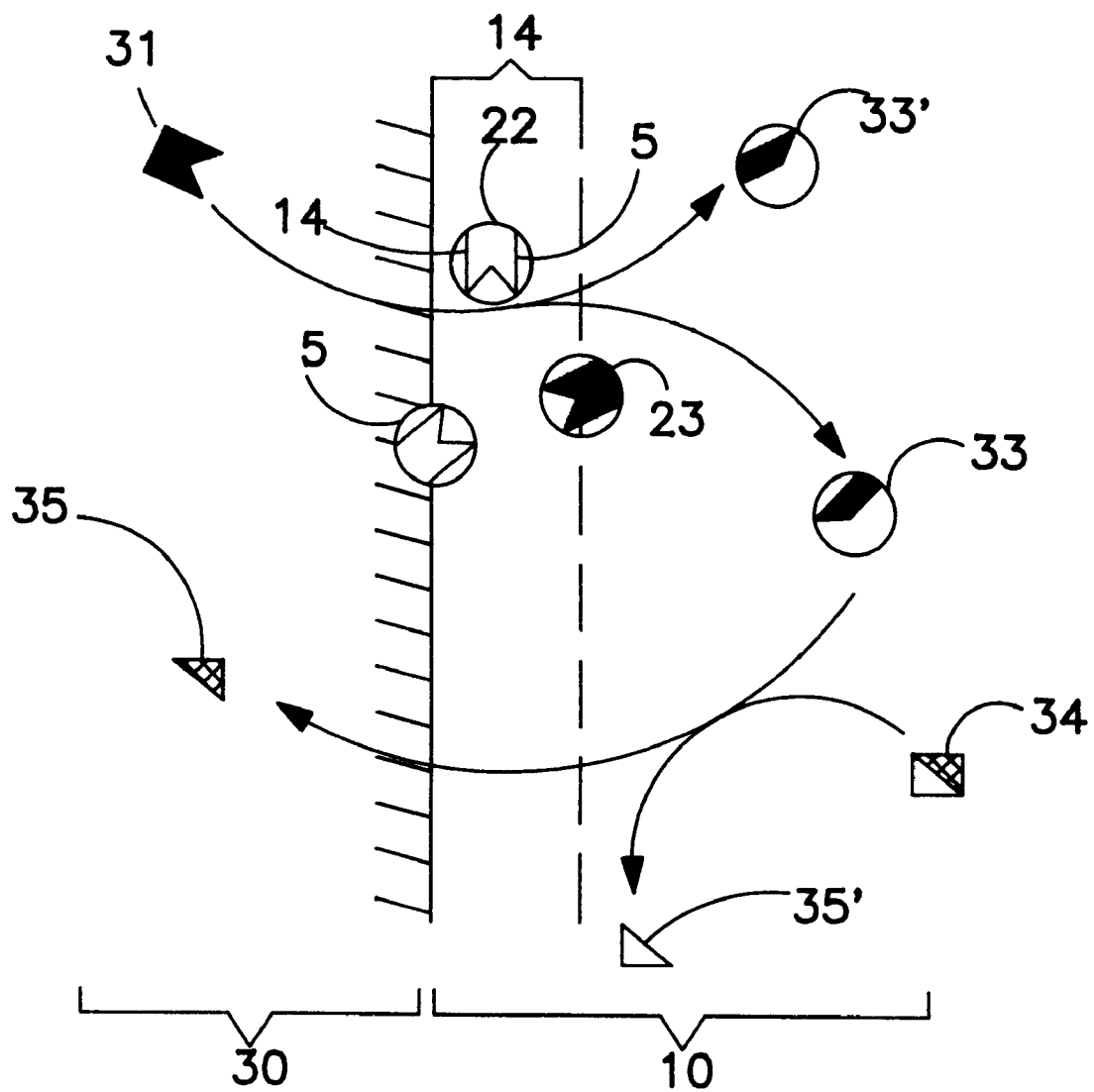
FIG. 5 is a schematical representation of a recognition step of the first kind coupled to a recognition step of the second kind in a layer.

FIG. 5 is a schematical representation of a recognition step of the first kind coupled to a recognition step of the second kind in a layer. The substance 31 of the sample 30 combines with the recognition component 5 in a recognition step of the first kind to form the occupied micelle 23. This will lead to products 33 and 33'. The recognition component 5 is part of the micellar recognition system and is located in the reactive region 14 of layer 10 in the unoccupied micelle 22. In a recognition step of the second kind the product 33 leads to the transformation of another recognition component 34 in the course of a further reaction, giving rise to second products 35 and 35'. The recognition component 34 may be distributed in any convenient way in the layer 10, including the reactive region 14, for instance, in the micelle or the phase surrounding the micelle, i.e., either in the lipophilic or in the hydrophilic phase. The second product 35 may move back into the sample 30, at least partly, or it may be leached from the layer 10 by the sample 30, or, as second product 35', it may disperse, at least partly, in the layer 10 in an empty or any other micelle, or anywhere in the layer. The recognition step of the second kind is part of the transducing process and leads to the formation of the measurement variable.

5. EXAMPLES

Example 1 describes a layer structure of a micellar urea biooptode.

The components which were chosen for the micellar recognition system were cyclohexanone (lipophilic phase), AOT (surface-active substance), $H_2O$ (hydrophilic phase), urease (recognition component).

Formation of the micellar recognition system was effected in accordance with Procedure D (step 1):

(a) Formation of a first mixture: 1.7 ml of a 25 mM AOT solution in cyclohexanone. Further addition of 1.8 mg nonactin (ionophore as first recognition component of the second kind), 1.3 mg chromoionophore ETH 5350 (indicator as second recognition component of the second kind).

(b) Formation of a second mixture: aqueous solution of urease, where 20 mg urease were solubilized in 100 μl water, corresponding to 1'600 units.

(c) 60 μl of the aqueous urease solution of the second mixture were added to the first mixture, yielding a $W_o$ value of 78.4.

(d) After vortex (centrifugal vibration mixer) a homogeneous mixture was obtained.

Incorporation of the micellar recognition system into the layer structure was effected as following (step 2):

88 mg PVC (polymer) and 170 mg ortho-NPOE (ortho-nitrophenyloctylether, plasticizer) and 2.5 mg NaTFPB (sodium-tetrakis(3,5-bis(trifluoromethyl)-phenyl)borate, additive) were added to 1.7 ml of the homogeneous mixture. After stirring and short temperature increase to 30° C. a clear, viscous mixture was obtained, i.e., the so-called cocktail.

0.3 ml cocktail were applied on a quartz support in a spin-on apparatus (Seiler, K., Simon, W., Anal. Chim. Acta, 266, 1992, 74). On evaporation of the organic solvent a layer of a thickness of 2 to 4 μm was obtained. The layer was dried at room temperature for 4 hours, constituting the layer structure itself, as no additional layers were required for formation of the layer structure.

Contacting the substance with the layer structure (step 3)

Two quartz supports coated with the layer structure were fixed in a flow cell of a double-beam spectrophotometer (Uvikon 942), which was mounted on a 25° C. thermostat-controlled base plate in the measuring channel. The layer structure was conditioned with 30 mN sodium phosphate buffer solution (pH 7.1). Measurements were made on various concentrations of buffered solutions of urea, with urea as target substance. The change in extinction (measurement variable) at the absorption maximum of the protonated form of the chromoionophore ETH 5350 was monitored at 652 nm, with readings as following;

| [Urea] | 0 | 0.001M | 0.01M | 0.1M |
|---|---|---|---|---|
| Extinction (652 nm) | 0.136 | 0.118 | 0.080 | 0.052 |

Following is a description of the functioning of the micellar urea biooptode.

Selective recognition of urea by the urease enzyme in a micellar recognition system (step 4) is coupled with an optical transducing step (step 5) (optode). The response behavior of such a sensor is based on an ion exchange-equilibrium-mechanism as following. Corresponding to the water content of the micelle and the working pH, the enzymatically catalyzed hydrolysis of urea (see reaction 1) will give rise to $NH_4^+$ ions or ammonia ($NH_3$), which are complexed by the ionophore nonactin (L) in a recognition step of the second kind. Subsequent to complexing deprotonation of the indicator ($H^+$-selective chromoionophore ETH 5350) will take place according to reaction 2.

Reaction 1: recognition step of the first kind

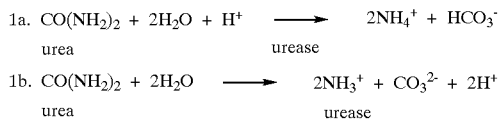

Reaction 2: transducing step (ion exchange equilibrium)

2a. $NH_4^+{}_{aq}+L+IndH^++R^- \rightleftharpoons LNH_4^++Ind+R^-+H^+{}_{aq}$

2b. $NH_{3aq}+L+IndH^++R^- \rightleftharpoons LNH_4^++Ind+R^-$

The total cation concentration in the electrically neutral layer is determined by the ionic additive $R^-$. The measured variable obtained from the transducing step (step 6) refers to the deprotonation of the indicator and the change in extinction connected therewith, via which the information on the substance, or urea activity, is obtained. To exclude interfering cations the layer may be coated with a cationic auxiliary layer. In this way a layer structure is formed.

Example 2 describes a layer structure of a micellar α-chymotrypsin optode.

The components which were chosen for the micellar recognition system were cyclohexane (lipophilic phase), AOT (surface-active substance), $H_2O$ (hydrophilic phase), α-chymotrypsin (recognition component).

Formation of the micellar recognition system was effected in accordance with Procedure A (step 1):

(a) Formation of a first mixture: 1.5 ml of a 25 mM AOT solution in cyclohexane.

(b) Formation of a second mixture: aqueous solution of α-chymotrypsin, where 18 mg α-chymotrypsin were solubilized in 100 μl water.

(c) 20 μl of the aqueous α-chymotrypsin solution of the second mixture were added to the first mixture, resulting in a $W_o$ value of 25.0.

(d) After vortex (centrifugal vibration mixer) a homogeneous mixture was obtained.

Incorporation of the micellar recognition system into the layer structure was effected as following (step 2):

120 mg PSB (polystyrene butadiene, polymer) and 87 mg BBPA (bis(1-butylpentyl)adipate, plasticizer) were added to 1.5 ml of the homogeneous mixture. After stirring a clear, viscous mixture was obtained, i.e., the so-called cocktail.

0.3 ml cocktail were applied on a quartz support in a spin-on apparatus (Seiler, K., Simon, W., Anal. Chim. Acta, 266, 1992, 74). On evaporation of the cyclohexane a layer of a thickness of 2 to 5 μm was obtained. The layer was dried at room temperature for 3 hours, constituting the layer structure itself, as no additional layers were required for formation of the layer structure.

Contacting the substance with the layer structure (step 3)

Two quartz supports coated with the layer structure were fixed in a flow cell of a double-beam spectrophotometer (Uvikon 942), which was mounted on a 25° C. thermostat-controlled base plate in the measuring channel. The layer structure was conditioned with 50 mN tris buffer solution (pH 8.0). Measurements were made on various concentrations of buffered Ac-Trp-ONp solutions (acetyl-L-tryptophane-p-nitrophenyl ester), with AC-Trp-ONp as target substance. The change in extinction (measurement variable) was monitored at 652 nm.

Following is a description of the functioning of the micellar α-chymotrypsin biooptode.

Selective recognition of Ac-Trp-ONp (acetyl-L-tryptophane-p-nitrophenyl ester) by the α-chymotrypsin enzyme in a micellar recognition system (step 4) is directly effected by a spectrophotometric process. In this instance no further recognition components are required. During the enzymatically catalyzed hydrolysis of Ac-Trp-ONp the product p-nitrophenol (p-Np) is produced, which is measured spectrophotometrically at 400 nm (step 5).

1. Recognition step of the first kind

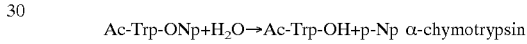

Ac-Trp-ONp+$H_2O \rightarrow$ Ac-Trp-OH+p-Np  α-chymotrypsin

2. Transducing step

The transducing step is effected by direct spectrophotometric detection of the resulting product p-nitrophenol (p-Np) at 400 nm.

The measured variable obtained with the transducing step (step 6) is the change in extinction at 400 nm, via which the information on the substance, or concentration of Ac-Trp-ONp is obtained.

Example 3 describes a layer structure of a micellar immunosensor.

The components which were chosen for the micellar recognition system were cyclohexane (lipophilic phase), AOT (surface-active substance), $H_2O$ (hydrophilic phase), Anti-Maus IgG (recognition component).

Formation of the micellar recognition system was effected in accordance with Procedure A (step 1):

(a) Formation of a first mixture: 1.5 ml of a 25 mM AOT solution in cyclohexane.

(b) Formation of a second mixture: aqueous solution of Anti-Maus IgG, where 1.8 mg Anti-Maus IgG was solubilized in 1,000 μl water.

(c) 23 μl of the second mixture were added to the first mixture, resulting in a $W_o$ value of 30.

(d) After vortex (centrifugal vibration mixer) a homogeneous mixture was obtained.

Incorporation of the micellar recognition system into the layer structure was effected as following (step 2):

120 mg PSB (polystyrene butadiene, polymer) and 87 mg BBPA (bis(1-butylpentyl)adipate, plasticizer) were added to 1.5 ml of the homogeneous mixture. After stirring a clear, viscous mixture was obtained, i.e., the so-called cocktail.

0.3 ml cocktail were applied on one side of a sapphire mono-crystal in a spin-on apparatus (Seiler, K., Simon, W., Anal. Chim. Acta, 266, 1992, 74). The sapphire monocrystal acting as an optical waveguide had the dimensions 5 cm×2 cm×1 mm, its angles at the edges were 60° and 120°. On evaporation of the cyclohexane a layer of a thickness of 2 to 5 μm was obtained. The layer was dried at room temperature for 4 hours, constituting the layer structure itself, as no additional layers were required for formation of the layer structure.

Contacting the substance with the layer structure (step 3)

The layer structure on the crystal was fixed in a specially made ATR measuring cell. Measurements were performed in a double-beam photometer with air as a reference. The layer structure was conditioned with 50 mN tris buffer solution (pH 8.0). Buffered solutions of the Maus IgG protein constituting the target substance were brought into contact with the layer structure in various concentrations. The change in the refractive index (measurement variable) of the layer structure was measured.

Following is a description of the functioning of the micellar immunosensor.

Selective recognition of the protein Maus-IgG (antigen), which is often used as a model for the large number of monoclonal antibodies produced by cell culturing, is effected by the Anti-Maus IgG antibody in a micellar recognition system (step 4). The immune reaction between antigen and antibody is directly measured with the use of the ATR (attenuated total reflection) method. This change in the refractive index (measurement variable) of the layer structure, or rather, the rate of this change, is measured after contact with the antigen sample has been established, and is proportional to the antigen concentration of the sample.

It goes without saying that the method of the invention is not restricted to the determination of urea, α-chymotrypsin and Maus-IgG. There are a great number of industrial applications, some of which are listed below.

Such a method and the respective layer structures may be used in pharmaceutical, medical and clinical-chemical analysis and in environmental technology for determination of immunochemical interactions; in clean-room monitoring, chemical process technology, biotechnology, drinking and waste water control.

Other applications are found in agricultural technology, e.g., the storage of fruit and crops, where monitoring of the atmosphere in cold-storage facilities via control of the composition of gases is of prime importance. Further uses in agricultural technology or in food processing are concerned with the employment of smell sensors for recognition of aromatic substances in the vapor-phase for the purpose of fruit classification.

In the textile industry potential uses emerge in the context of sweat analysis in sports textiles.

Applications in construction technology include the analysis of heavy metals, chlorides and microorganisms in concrete and masonry of all types; interesting issues in building maintenance are ventilation, air exchange rates and determination of the $CO_2$ content.

Uses in the detergent and tenside industry include the monitoring of tensides in effluent control; in pharmaceutical research, drug manufacture and control, the method and structure of the invention could be used to determine interactions between active substances and receptors.

The above list serves to indicate a wide variety of uses, but is in no way exhaustive.

The essential characteristics of the invention are that with the method and corresponding layer structures described by the invention a micellar recognition system is formed from a recognition component in a suitable manner. This micellar recognition system is incorporated into a layer structure so that it is provided in the layer structure as a single layer. The recognition component exhibits an extended life, and the entire layer structure improved durability as a consequence. Special advantages of such layer structures are their higher sensitivity, lower detection threshold, short response time, repeated usability and special robustness with regard to sample interference.

We claim:

1. A method for determination of a substance, comprising the steps of:

(1) forming at least one micellar recognition system, into which is incorporated at least one recognition component specific for said substance, wherein the micellar recognition system is formed from two non-miscible phases, at least one surface-active substance, and at least one recognition component, (2) incorporating the micellar recognition system into a layer structure in which it forms at least one single layer, (3) bringing the layer structure provided in step (2) into contact with the substance to be determined, (4) having at least one recognition step which takes place in said single layer, (5) having said recognition step followed by at least one transducing step, and (6) producing at least one measurement variable as a consequence, and obtaining at least one information on the substance with said measurement variable.

2. A method according to claim 1, wherein the physical and chemical properties of the at least one single layer are adjusted by means of viscosity-controlling additives and plasticizers.

3. A method according to claim 1, wherein the recognition component which leads to a recognition step of a first kind, selectively recognizes the substance.

4. A method according to claim 1, including a step of forming auxiliary layers over said at least one single layer.

5. A method according to claim 1, wherein the substance is constituted by ions, charged, uncharged or neutral molecules, isotopes, microorganisms, viruses, organelles, salts or receptors.

6. A method according to claim 1, wherein the information on the substance is obtained in the form of an amount, or a concentration, or counted result, or as an activity.

7. A method according to claim 1, wherein the recognition component leads to a recognition step of a first kind and induces a transducing step.

8. A method according to claim 1, wherein the recognition component leads to a recognition step of a second kind and thus to a transducing process, and triggers at least one further reaction, and which starts from a product of the recognition step of a first kind.

* * * * *